US012758681B2

(12) United States Patent
Chen et al.

(10) Patent No.: US 12,758,681 B2
(45) Date of Patent: Oct. 13, 2026

(54) TITANIUM IMPLANT WITH SURFACE COATING IN CRATER-LIKE POROUS SHAPE AND PREPARATION METHOD THEREOF, AND IMPLANT MATERIAL

(71) Applicant: Shanghai Ruizhikang Medical Technology Co., Ltd., Shanghai (CN)

(72) Inventors: Xiaohong Chen, Shanghai (CN); Binbin Kang, Shanghai (CN); Fengcang Ma, Shanghai (CN); Shaoli Fu, Shanghai (CN); Haochen Wu, Shanghai (CN)

(73) Assignee: Shanghai Ruizhikang Medical Technology Co., Ltd., Shanghai (CN)

( * ) Notice: Subject to any disclaimer, the term of this patent is extended or adjusted under 35 U.S.C. 154(b) by 562 days.

(21) Appl. No.: 18/146,497

(22) Filed: Dec. 27, 2022

(65) Prior Publication Data

US 2024/0139370 A1 May 2, 2024

(30) Foreign Application Priority Data

Oct. 28, 2022 (CN) ........................ 202211336906.1

(51) Int. Cl.
*C25D 11/26* (2006.01)
*A61L 27/06* (2006.01)
*A61L 27/56* (2006.01)
*C25D 11/02* (2006.01)

(52) U.S. Cl.
CPC ............... *A61L 27/06* (2013.01); *A61L 27/56* (2013.01); *C25D 11/022* (2013.01); *C25D 11/026* (2013.01); *C25D 11/26* (2013.01); *A61L 2420/02* (2013.01)

(58) Field of Classification Search
None
See application file for complete search history.

(56) References Cited

U.S. PATENT DOCUMENTS

2018/0280143 A1* 10/2018 Gorhe ................. C25D 11/026

OTHER PUBLICATIONS

English translation CN 113897652 (Year: 2022).*
English translation CN 114921832 (Year: 2022).*
English translation CN 103083099 (Year: 2013).*
(Continued)

*Primary Examiner* — Stefanie S Wittenberg
(74) *Attorney, Agent, or Firm* — Daniel A. Thomson; Emerson Thomson Bennett®, LLC

(57) ABSTRACT

The present disclosure provides a preparation method of a titanium implant with a surface coating in a crater-like porous shape. A titanium substrate is subjected to polishing, cleaning, and first drying in sequence to obtain a pretreated titanium substrate. This step eliminates an influence of roughness and surface impurities of the titanium substrate on roughness and a structure of a coating formed on a surface of the titanium substrate after micro-arc oxidation, so as to obtain a titanium implant with a specific structure and a desirable biological performance. The micro-arc oxidation is conducted using the pretreated titanium substrate as an anode and iron as a cathode in an electrolyte containing sodium phosphate. In this step, a micro-arc oxidation coating is formed on the surface of the titanium substrate to obtain the titanium implant with a surface coating in a crater-like porous shape.

4 Claims, 9 Drawing Sheets

(56) References Cited

OTHER PUBLICATIONS

English translation CN 115012014 (Year: 2022).*
English translation CN105603488 (Year: 2016).*
Kang et al., "Evaluation of antibacterial property and biocompatibility of Cu doped TiO2 coated implant prepared by micro-arc oxidation", Front. Bioeng. Biotechnol., Aug. 2022. (Year: 2022).*

* cited by examiner

TITANIUM IMPLANT WITH SURFACE COATING IN CRATER-LIKE POROUS SHAPE AND PREPARATION METHOD THEREOF, AND IMPLANT MATERIAL

CROSS REFERENCE TO RELATED APPLICATION

This patent application claims the benefit and priority of Chinese Patent Application No. 202211336906.1, filed with the China National Intellectual Property Administration on Oct. 28, 2022, the disclosure of which is incorporated by reference herein in its entirety as part of the present application.

TECHNICAL FIELD

The present disclosure relates to the technical field of biomedical materials, in particular to a titanium implant with a surface coating in a crater-like porous shape and a preparation method thereof, and an implant material.

BACKGROUND

Pure titanium has desirable biocompatibility and corrosion resistance in oral implants. Due to the low biological activity and the long period of "osseointegration" in clinical applications, it is necessary to modify the surface of pure titanium in order to improve the bioactivity of the surface of pure titanium and reduce the period of osseointegration.

In the prior art, common treatment methods for the surface of titanium implants are as follows: (1) acid etching: the acid etching is a common method for surface roughening, and can form irregular micron-level roughness on the surface of the implant. The method increases a surface area of the implant, which is beneficial to the attachment and growth of cells. However, acid etching may produce waste acid to cause environmental pollution. (2) Anodizing: the anodizing is a traditional metal surface treatment method, which belongs to the electrochemical treatment, showing low cost and clear effect. However, after anodizing, the coating and the substrate have a poor bonding force, which is easy to be peeled off. Therefore, there is an urgent need for a treatment method for the surface of titanium implants that is environmental-friendly, such that the treated coating and the substrate have a strong bonding force, which is not easy to be peeled off.

SUMMARY

An objective of the present disclosure is to provide a titanium implant with a surface coating in a crater-like porous shape and a preparation method thereof, and an implant material. In the present disclosure, the preparation method is environmental-friendly, and can prepare a phosphorus-containing coating with a crater-like porous shape on the surface of the titanium implant; the coating has a strong bonding force with the substrate (the titanium implant), which is not easy to be peeled off.

To achieve the above objective, the present disclosure provides the following technical solutions.

The present disclosure provides a preparation method of a titanium implant with a surface coating in a crater-like porous shape, including the following steps:

(1) subjecting a titanium substrate to polishing, cleaning, and first drying in sequence to obtain a pretreated titanium substrate; and (2) conducting micro-arc oxidation using the pretreated titanium substrate obtained in step (1) as an anode and iron as a cathode in an electrolyte containing sodium phosphate to obtain the titanium implant with a surface coating in a crater-like porous shape.

Preferably, in step (1), the titanium substrate is a TA4 titanium alloy.

Preferably, in step (1), the polishing is conducted by: polishing the titanium substrate with sandpapers of 400 #, 800 #, 1200 #, 2000 #, and 3000 # in sequence.

Preferably, in step (1), the cleaning is conducted by ultrasonic cleaning with acetone, absolute ethanol, and deionized water in sequence.

Preferably, in step (2), the electrolyte containing sodium phosphate has a temperature of 6° C. to 20° C.

Preferably, in step (2), the micro-arc oxidation is conducted at a current of 1.2 A to 2 A and a working frequency of 400 Hz to 600 Hz.

Preferably, in step (2), the micro-arc oxidation is conducted at a duty ratio of 3% to 35% for 2 min to 15 min.

Preferably, in step (2), after the micro-arc oxidation is completed, a micro-arc oxidation product is subjected to rinsing and second drying in sequence.

The present disclosure further provides a titanium implant with a surface coating in a crater-like porous shape prepared by the preparation method.

The present disclosure further provides an implant material including the titanium implant with a surface coating in a crater-like porous shape.

The present disclosure provides a preparation method of a titanium implant with a surface coating in a crater-like porous shape. A titanium substrate is subjected to polishing, cleaning, and first drying in sequence to obtain a pretreated titanium substrate. This step eliminates an influence of roughness and surface impurities of the titanium substrate on roughness and a structure of a coating formed on a surface of the titanium substrate after micro-arc oxidation, so as to obtain a titanium implant with a specific structure and a desirable biological performance. The micro-arc oxidation is conducted using the pretreated titanium substrate as an anode and iron as a cathode in an electrolyte containing sodium phosphate. In this step, a micro-arc oxidation coating is formed on the surface of the titanium substrate to obtain the titanium implant with a surface coating in a crater-like porous shape. Moreover, in the present disclosure, a main component of the micro-arc oxidation coating prepared by the method is a titanium dioxide porous layer, which has a densely-distributed crater-like porous structure, high porosity, and superhydrophilicity. The coating can significantly enhance a cell adsorption and proliferation ability on the surface of the titanium implant, such that a prepared dental implant has high biocompatibility, improving an osseointegration rate of the oral implant, shortening a treatment time, and improving a success rate. In addition, a microscopic appearance of the micro-arc oxidation coating is crater-shaped, with different pore sizes, forming a certain roughness, which can promote cell adhesion and can also induce bone tissues to bond with the coating. The coating improves the osseointegration rate and increases the firmness between the bone tissues and coating, such that the titanium implant is suitable for dental implants for repairing dentition defects or missing dentition in clinical stomatology. The thickness of the coating can make a bonding strength of the medical titanium substrate better, which can prevent the porous layer from affecting clinical application due to peeling off from the surface of titanium substrate after the titanium implant is implanted into the body for a period of time. The porous micro-arc oxidation coating (belonging to a ceramic film layer) contains Ti, O, P and other elements, where phosphorus has an excellent biological activity, which serves as a main inorganic component in mature bone, and plays a highly important role in promoting bone formation. The micro-arc oxidation coating has excellent hydrophilicity, can quickly promote the penetration of fluid in the body into the implant during repair of missing or defective teeth, and can also stabilize blood clots, followed by organized bone formation. The porous micro-arc oxidation coating is composed of amorphous and partial anatase crystal phase $TiO_2$, and the anatase phase $TiO_2$ shows relatively desirable compatibility with blood, such as red blood cells and platelets. Furthermore, the preparation method has a simple process and mild reaction conditions, which is suitable for large-scale production, showing desirable application prospects in the field of dental implants. The results of examples show that after being treated by the method of the present disclosure, a porous layer formed on a surface of a medical titanium substrate (the titanium implant) prepared in Example 1 can significantly enhance the adhesion, proliferation, and differentiation of osteoblasts. The porous layer prepared in Example 1 has a crater-like porous shape with a pore size of about 6 μm, which is conducive to the adhesion and growth of bone-derived cells, and has a great effect on the growth of osteoblasts; an adhesion level of the porous layer is 5B, showing a relatively-high bonding strength with the titanium substrate. The porous layer prepared in Example 1 and the titanium substrate have a bonding strength of 5.9N. The porous layer prepared in Example 1 has a thickness of 3 μm to 10 μm, where the crater-like porous shape has a convex part with a thickness of about 10 μm, and a concave part with a thickness of about 3 μm; the porous layer is mainly composed of Ti, O, P and other elements, showing an excellent biological activity. The porous layer prepared in Example 1 has medium roughness, with an Ra value of (1.399±0.008) μm. The porous layer prepared in Example 1 has a contact angle of (43.75±0.89)°.

DETAILED DESCRIPTION OF THE EMBODIMENTS

Figure 1:
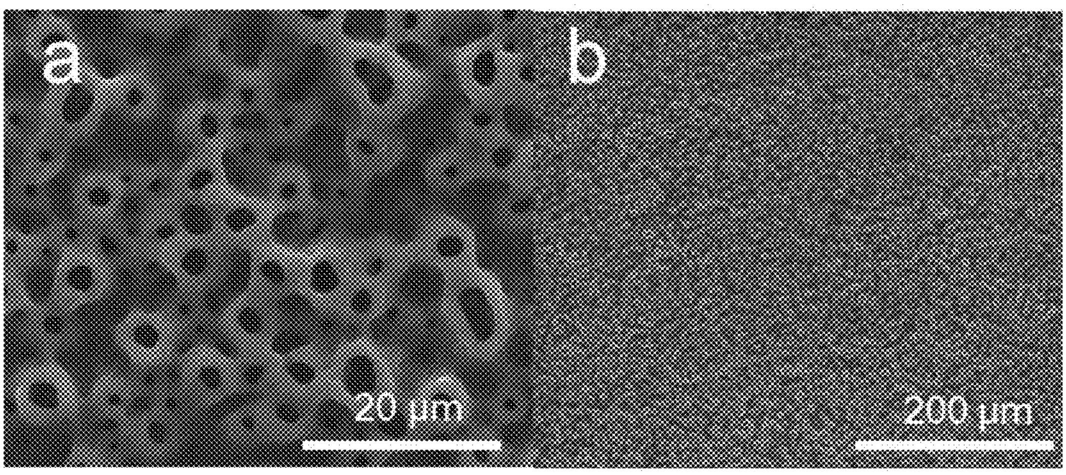
FIG. 1 shows a surface structure of a porous layer on a surface of a titanium implant with a surface coating in a crater-like porous shape prepared in Example 1 of the present disclosure.

The present disclosure provides a preparation method of a titanium implant with a surface coating in a crater-like porous shape, including the following steps:

(1) subjecting a titanium substrate to polishing, cleaning, and first drying in sequence to obtain a pretreated titanium substrate; and (2) conducting micro-arc oxidation using the pretreated titanium substrate obtained in step (1) as an anode and iron as a cathode in an electrolyte containing sodium phosphate to obtain the titanium implant with a surface coating in a crater-like porous shape.

In the present disclosure, unless otherwise specified, all raw materials used are commercially available products conventional in the art.

In the present disclosure, a titanium substrate is subjected to polishing, cleaning, and first drying in sequence to obtain a pretreated titanium substrate.

In the present disclosure, the titanium substrate is preferably a TA4 titanium alloy; and the titanium substrate is preferably in the form of flakes. The TA4 titanium alloy is used as the titanium substrate to increase a tensile strength and obtain a titanium implant with a surface coating in a crater-like porous shape, showing better comprehensive performances.

In the present disclosure, in step (1), the polishing is conducted preferably by: polishing the titanium substrate with sandpapers of 400 #, 800 #, 1200 #, 2000 #, and 3000 # in sequence. The polishing eliminates an influence of the roughness and surface impurities of the titanium substrate on the roughness and structure of the coating formed on the surface of the titanium substrate after micro-arc oxidation, thereby obtaining a titanium implant with a specific structure and desirable biological performances. The polishing is conducted by preferably a metallographic grinding and polishing machine.

In the present disclosure, the cleaning is conducted preferably by ultrasonic cleaning with acetone, absolute ethanol, and deionized water in sequence. The ultrasonic cleaning with acetone is conducted for preferably 3 min to 35 min, more preferably 5 min to 30 min. The ultrasonic cleaning with absolute ethanol is conducted for preferably 3 min to 35 min, more preferably 5 min to 30 min. The ultrasonic cleaning with deionized water is conducted for preferably 3 min to 35 min, more preferably 5 min to 30 min.

In the present disclosure, the first drying is conducted at preferably 35° C. to 70° C., more preferably 40° C. to 60° C. The first drying is conducted for preferably 25 min to 130 min, more preferably 30 min to 120 min.

In the present disclosure, micro-arc oxidation is conducted using the pretreated titanium substrate as an anode and iron as a cathode in an electrolyte containing sodium phosphate to obtain the titanium implant with a surface coating in a crater-like porous shape.

In the present disclosure, the electrolyte containing sodium phosphate has a temperature of preferably 6° C. to 20° C., more preferably 8° C. to 18° C. The temperature of the electrolyte containing sodium phosphate is controlled in the above-mentioned range, to promote a smooth progress of the micro-arc oxidation, to prevent the electrolyte from having a temperature that is too high or too low during the micro-arc oxidation to affect the roughness and structure of the micro-arc oxidation coating formed by the micro-arc oxidation, thereby obtaining a titanium implant with a surface coating in a crater-like porous shape, showing better comprehensive performances.

In the present disclosure, a solvent of the electrolyte containing sodium phosphate is preferably deionized water; and a solute of the electrolyte containing sodium phosphate includes preferably sodium phosphate, glycerol, and potassium hydroxide.

In the present disclosure, the sodium phosphate-containing electrolyte has the sodium phosphate with a concentration of preferably 15 g/L to 25 g/L, more preferably 18 g/L to 22 g/L, and even more preferably 20 g/L. The sodium phosphate is used as the solute of the electrolyte containing sodium phosphate at a concentration in the above-mentioned range, and the sodium phosphate is dissolved in water, hydrolyzes to generate OH—, improving solution conductivity; the P element in sodium phosphate enters the micro-arc oxidation coating after micro-arc oxidation, where P is a biological functional ion, which improves a biological activity of the micro-arc oxidation coating.

In the present disclosure, the sodium phosphate-containing electrolyte has potassium hydroxide with a concentration of preferably 2 g/L to 8 g/L, more preferably 3 g/L to 6 g/L, and even more preferably 4 g/L. The potassium hydroxide is used as the solute of the electrolytic containing sodium phosphate at a concentration in the above-mentioned range, and the potassium hydroxide provides OH—, increasing conductivity of the electrolyte; it is avoided that the concentration of potassium hydroxide is too high or too low to affect the structure of the micro-arc oxidation coating, thereby affecting the quality of the micro-arc oxidation coating.

In the present disclosure, the sodium phosphate-containing electrolyte has glycerol with a concentration of preferably 3 mL/L to 10 mL/L, more preferably 4 mL/L to 7 mL/L, more preferably 5 mL/L. The glycerol is used as the solute of the electrolyte containing sodium phosphate at a concentration in the above-mentioned range, so as to suppress electric arc in the micro-arc oxidation; it is avoided that the concentration of glycerol is too high or too low to affect the quality of the micro-arc oxidation coating.

In the present invention, the iron is preferably an iron plate.

In the present disclosure, the micro-arc oxidation is conducted at a current of preferably 1.2 A to 2 A, more preferably 1.4 A to 1.7 A. The current of the micro-arc oxidation is controlled within the above range, so as to adjust the roughness and structure of the micro-arc oxidation coating, and obtain the micro-arc oxidation coating with the best porous morphology; it should be avoided that the current is too high to cause the formation of the coating sealing pores, and that the current is too low to cause the uneven distribution of the pores of the coating, thus finally obtaining a titanium implant with a surface coating in a crater-like porous shape, showing better comprehensive performances.

In the present disclosure, the micro-arc oxidation is conducted at a working frequency of preferably 400 Hz to 600 Hz, more preferably 450 Hz to 550 Hz, and even more preferably 500 Hz. The working frequency of the micro-arc oxidation is controlled within the above range, so as to adjust the roughness and structure of the micro-arc oxidation coating, and obtain the micro-arc oxidation coating with the best porous morphology, thus thereby obtaining a titanium implant with a surface coating in a crater-like porous shape, showing better comprehensive performances.

In the present disclosure, the micro-arc oxidation is conducted at a duty ratio of preferably 3% to 35%, more preferably 5% to 30%. The duty ratio of the micro-arc oxidation is controlled within the above range, so as to adjust the roughness and structure of the micro-arc oxidation coating, and obtain the micro-arc oxidation coating with the best porous morphology, thus thereby obtaining a titanium implant with a surface coating in a crater-like porous shape, showing better comprehensive performances.

In the present disclosure, the micro-arc oxidation is conducted for preferably 2 min to 15 min, more preferably 4 min to 10 min. The time of the micro-arc oxidation is controlled within the above range, so as to adjust the roughness and structure of the micro-arc oxidation coating, and obtain the micro-arc oxidation coating with the best porous morphology, thus thereby obtaining a titanium implant with a surface coating in a crater-like porous shape, showing better comprehensive performances. In the micro-arc oxidation, sodium phosphate, potassium hydroxide, and glycerol are used as electrolytes, and deionized water is used as a solvent to form a micro-arc oxidation-based electrolytic cell. With the principle of a primary battery, the titanium sheet is used as a cathode to undergo an oxidation reaction, and the iron plate is used as an anode to undergo a reduction reaction. The anions move to the cathode, the titanium sheet loses electrons and reacts with hydroxides to generate titanium dioxide and water, and water at the anode reacts to generate hydrogen and hydroxide, forming a MAO coating (the micro-arc oxidation coating) containing P, O, and Ti as main constituent elements on the surface of the titanium substrate. The MAO coating is divided into 3 stages due to an increase of voltage with time: an oxidation reaction occurs to form a thin film; the voltage increases, breaking down a weak area of the surface; and under the action of cooling water, a molten area is rapidly cooled to form a micro-arc oxidation coating with a densely-distributed and crater-like porous structure, thus obtaining a titanium implant with a surface coating in a crater-like porous shape.

In the present disclosure, after the micro-arc oxidation is completed, a micro-arc oxidation product is subjected to rinsing and second drying in sequence.

In the present disclosure, the rinsing is conducted by preferably deionized water. The rinsing is conducted preferably 3 to 5 times. The second drying is conducted at preferably 30° C. to 70° C., more preferably 40° C. to 60° C. The second drying is conducted for preferably 20 min to 140 min, more preferably 30 min to 120 min.

In the present disclosure, the preparation method of the titanium implant with a surface coating in a crater-like porous shape has a simple operation and mild reaction conditions, which is suitable for large-scale production.

The present disclosure further provides a titanium implant with a surface coating in a crater-like porous shape prepared by the preparation method.

The present disclosure further provides use of the titanium implant with a surface coating in a crater-like porous shape as an implant material.

The technical solutions of the present disclosure will be described below clearly and completely in conjunction with the examples of the present disclosure. Apparently, the described examples are only a part of, not all of, the examples of the present disclosure. All other embodiments obtained by those of ordinary skill in the art based on the embodiments of the present disclosure without creative efforts shall fall within the protection scope of the present disclosure.

Example 1

(1) A titanium substrate was subjected to polishing on a metallographic grinding and polishing machine with sandpapers of 400 #, 800 #, 1200 #, 2000 #, and 3000 # in sequence, a polished titanium substrate was subjected to ultrasonic cleaning with acetone, absolute ethanol, and deionized water in sequence, and then subjected to first drying in an oven at 40° C. for 30 min to obtain a pretreated titanium substrate; where the titanium substrate was a flaky TA4 titanium alloy; and the ultrasonic cleaning was conducted with the acetone for 5 min, and then the absolute ethanol for 5 min, and then the deionized water for 5 min; and (2) micro-arc oxidation was conducted using the pretreated titanium substrate obtained in step (1) as an anode and an iron plate as a cathode in an electrolyte containing sodium phosphate; after the micro-arc oxidation was completed, an obtained micro-arc oxidation product was rinsed 3 times with deionized water, and then dried in an oven at 40° C. for 30 min to obtain the titanium implant with a surface coating in a crater-like porous shape; where the electrolyte containing sodium phosphate had a temperature of 15° C.; and the micro-arc oxidation was conducted at a current of 1.4 A, a working frequency of 500 Hz, and a duty ratio of 5% for 4 min.

The electrolyte containing sodium phosphate used deionized water as a solvent, and sodium phosphate, glycerol, and potassium hydroxide as solutes; and the electrolyte containing sodium phosphate had the sodium phosphate of 20 g/L, potassium hydroxide of 4 g/L, and glycerol of 5 ml/L by concentration.

The porous layer (micro-arc oxidation coating) on the surface of the titanium implant with a surface coating in a crater-like porous shape prepared in Example 1 was subjected to the following detection or test, and the detection or test results were analyzed.

Test 1: Field-Emission Scanning Electron Microscope (FSEM) Test

Figure 2:
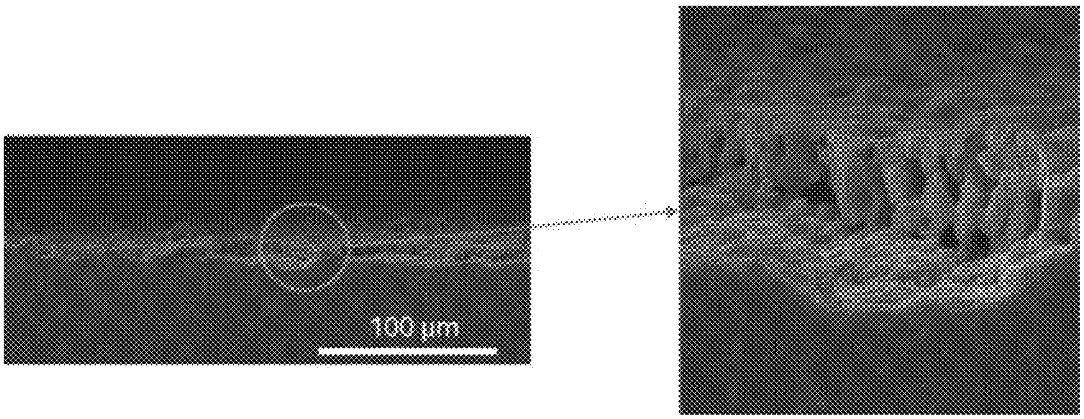
FIG. 2 shows a cross-sectional morphology of the porous layer on the surface of the titanium implant with a surface coating in a crater-like porous shape prepared in Example 1 of the present disclosure.
Figure 3:
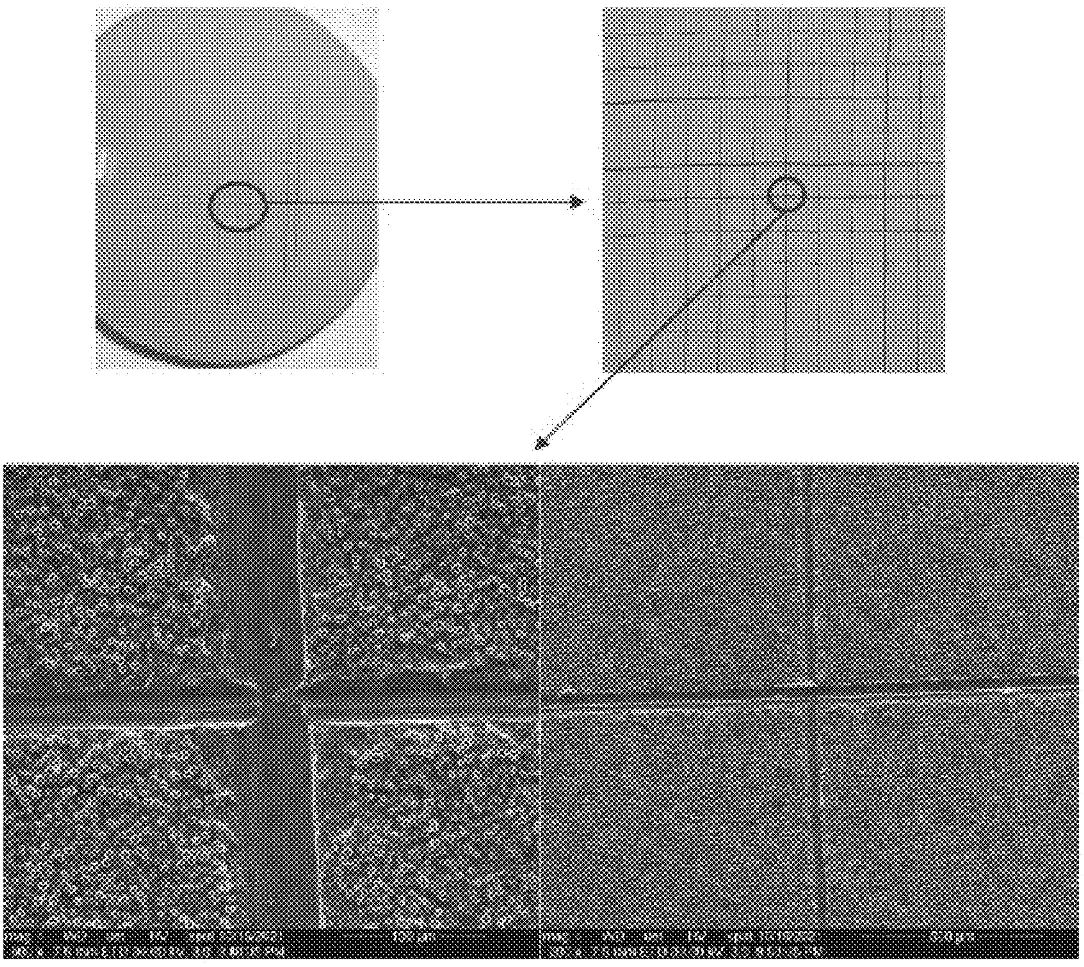
FIG. 3 shows a coating-substrate binding state of the porous layer on the surface of the titanium implant with a surface coating in a crater-like porous shape prepared in Example 1 of the present disclosure.
Figure 4:
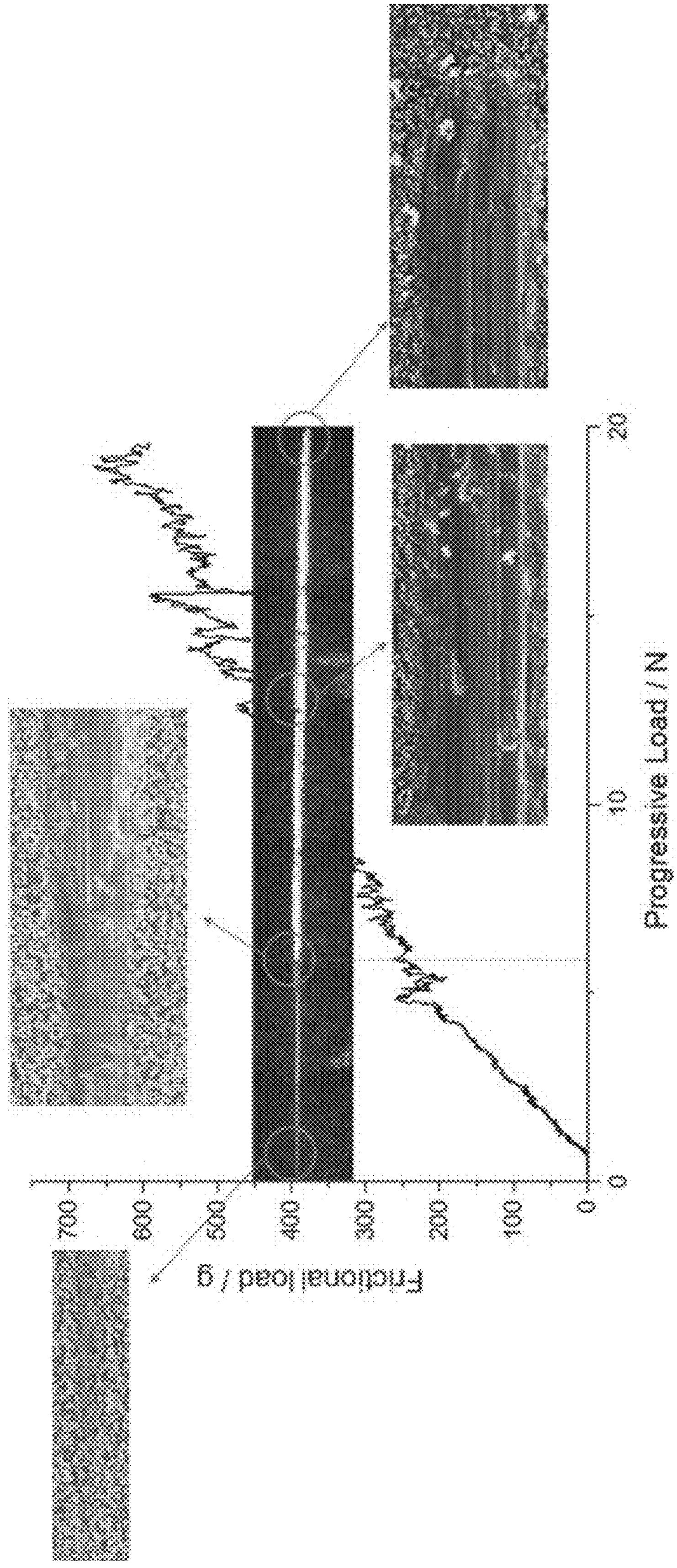
FIG. 4 shows a coating-substrate binding strength test of the porous layer on the surface of the titanium implant with a surface coating in a crater-like porous shape prepared in Example 1 of the present disclosure.
Figure 5:
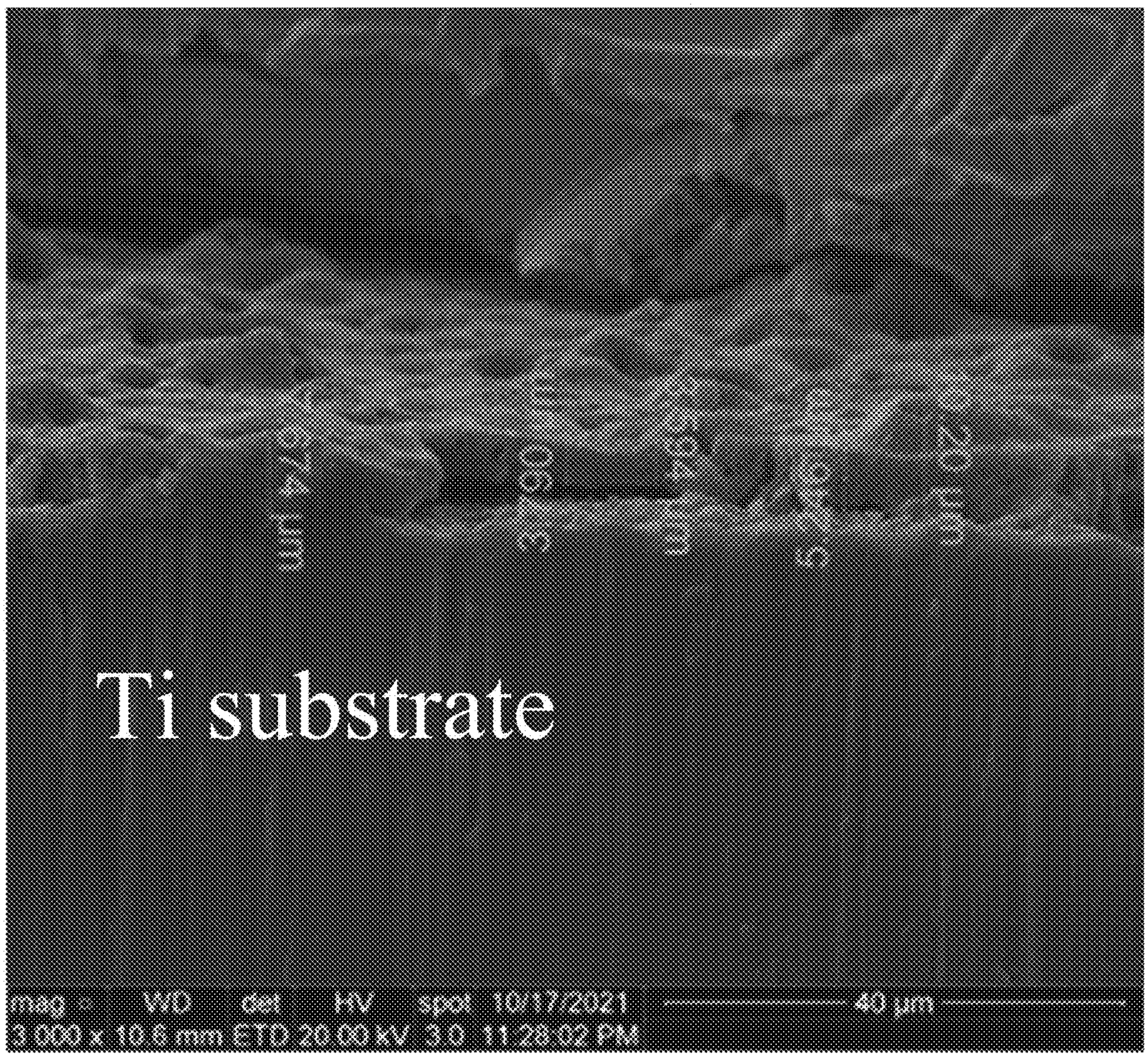
FIG. 5 shows a detection result of a coating thickness of the porous layer on the surface of the titanium implant with a surface coating in a crater-like porous shape prepared in Example 1 of the present disclosure.

With a Quanta FEG 450 FSEM, the detection and measurement were conducted on the porous layer, including surface structure, cross-sectional morphology, coating-substrate binding force, and membrane thickness. FIG. 1 showed the surface structure; FIG. 2 showed the cross-sectional morphology; FIG. 3 and FIG. 4 showed the coating-substrate binding state; and FIG. 5 showed a detection result of the coating thickness.

It was seen from FIG. 1 that the porous layer prepared in Example 1 had a crater-like porous shape with a pore diameter of about 6 μm. Studies had shown that at a micropore diameter of less than 10 μm, it was conducive to the adhesion and growth of bone-derived cells, showing a great effect on the growth of osteoblasts.

It was seen from FIG. 2 that the porous layer prepared in Example 1 was evenly distributed and had no obvious gap with the titanium substrate, indicating that there was a relatively high bonding strength between the porous layer and the titanium substrate.

It was seen from FIG. 3 that, according to ISO 2409 (2013), the coating bonding force was qualitatively analyzed, and the comparison showed that the porous layer prepared in Example 1 had an adhesion level of 5B. That is to say, the porous layer had a completely smooth notch, and there was no shedding phenomenon of the grid, confirming that the porous layer prepared in Example 1 had a high bonding strength with the titanium substrate.

From FIG. 4, it was seen that the coating/substrate binding force was quantitatively analyzed using a scratch tester. Combining an OM diagram of the scratch and the analysis of a dynamic load curve, it was concluded that the porous layer prepared in Example 1 and the titanium substrate have a bonding strength of 5.9 N.

It was seen from FIG. 5 that the porous layer prepared in Example 1 had a thickness of 3 μm to 10 μm, where the crater-like porous shape had a thickness of about 10 μm at a convex part, and a thickness of about 3 μm at a concave part; a thinner porous layer might significantly reduce the stress shielding of a high elastic modulus of pure titanium to the upper and lower alveolar bones. Therefore, the thin porous layer prepared in Example 1 facilitated the long-term stability of the implant for the restoration of tooth.

Test 2: Energy Spectrum Test

An energy spectrum matched with the Quanta FEG 450 FSEM was used to analyze the elemental composition and content of the porous layer prepared in Example 1, as shown in Table 1.

TABLE 1

Element arrangement and content of porous layer prepared in Example 1

| Element | Wt % | At % |
|---|---|---|
| O | 17.23 | 36.88 |
| P | 10.09 | 11.15 |
| Ti | 72.68 | 51.96 |

It was seen from Table 1 that after the titanium substrate in Example 1 was subjected to micro-arc oxidation, the porous layer formed on the surface was mainly composed of Ti, O, P and other elements. The P element came from the electrolyte, showing that the phosphorus contained in the sodium phosphate-containing electrolyte in Example 1 participated in the oxidation and film formation on the surface of the pure titanium anode. Phosphorus has a desirable biological activity, which is a main inorganic component in mature bone, and plays a highly important role in promoting bone formation.

Test 3: Roughness Test

Figure 6:
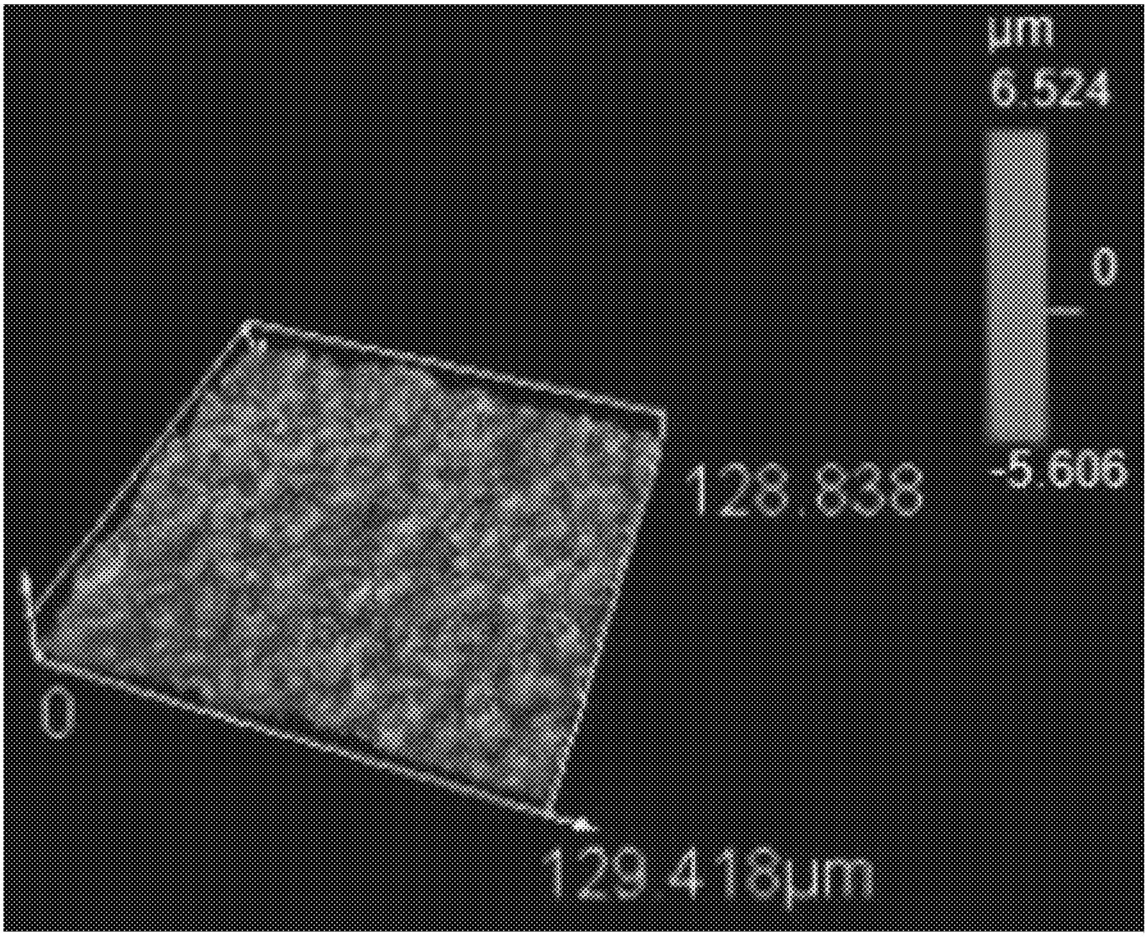
FIG. 6 shows a surface profile and a surface roughness diagram of the porous layer on the surface of the titanium implant with a surface coating in a crater-like porous shape prepared in Example 1 of the present disclosure.

A LEXT OLS4100 laser confocal scanner was used to detect the surface profile and surface roughness of the porous layer prepared in Example 1, and a surface profile and surface roughness map was obtained, as shown in FIG. 6.

It was seen from FIG. 6 that the porous layer prepared in Example 1 after the micro-arc oxidation had a medium roughness, that is, an Ra value was (1.399±0.008) μm. The porous layer with a certain roughness can reduce the occurrence of early fiber wrapping after medical pure titanium implantation, and can promote the deposition of phosphate salts, thereby increasing the osseointegration rate, and increasing the bonding strength between the implant and the alveolar bone to a certain extent. However, it has been found clinically that a greater roughness is more prone to peri-implantitis, and excessive roughness may also weaken cell proliferation. Therefore, the roughness of the porous layer prepared by the present disclosure can meet clinical requirements.

Test 4: XRD Test

An X-ray diffractometer was used to analyze the distribution of phase components in the ceramic film layer or porous layer (the micro-arc oxidation coating) prepared in Example 1 by the method. Scanning was conducted on a Cu target and Kα ray, at a tube voltage of 40 k, a tube current of 30 mA, and an incident wavelength of 0.154178 nm, with a scanning speed at 2.000°/min, and a diffraction angle range at 2θ=20° to 80°. By Jade6.5 software combined with PDF cards, the detection results of phase components were compared and analyzed. The composition of the phases in the porous layer prepared in Example 1 was finally determined, and an XRD pattern was obtained, as shown in FIG. 7.

Figure 7:
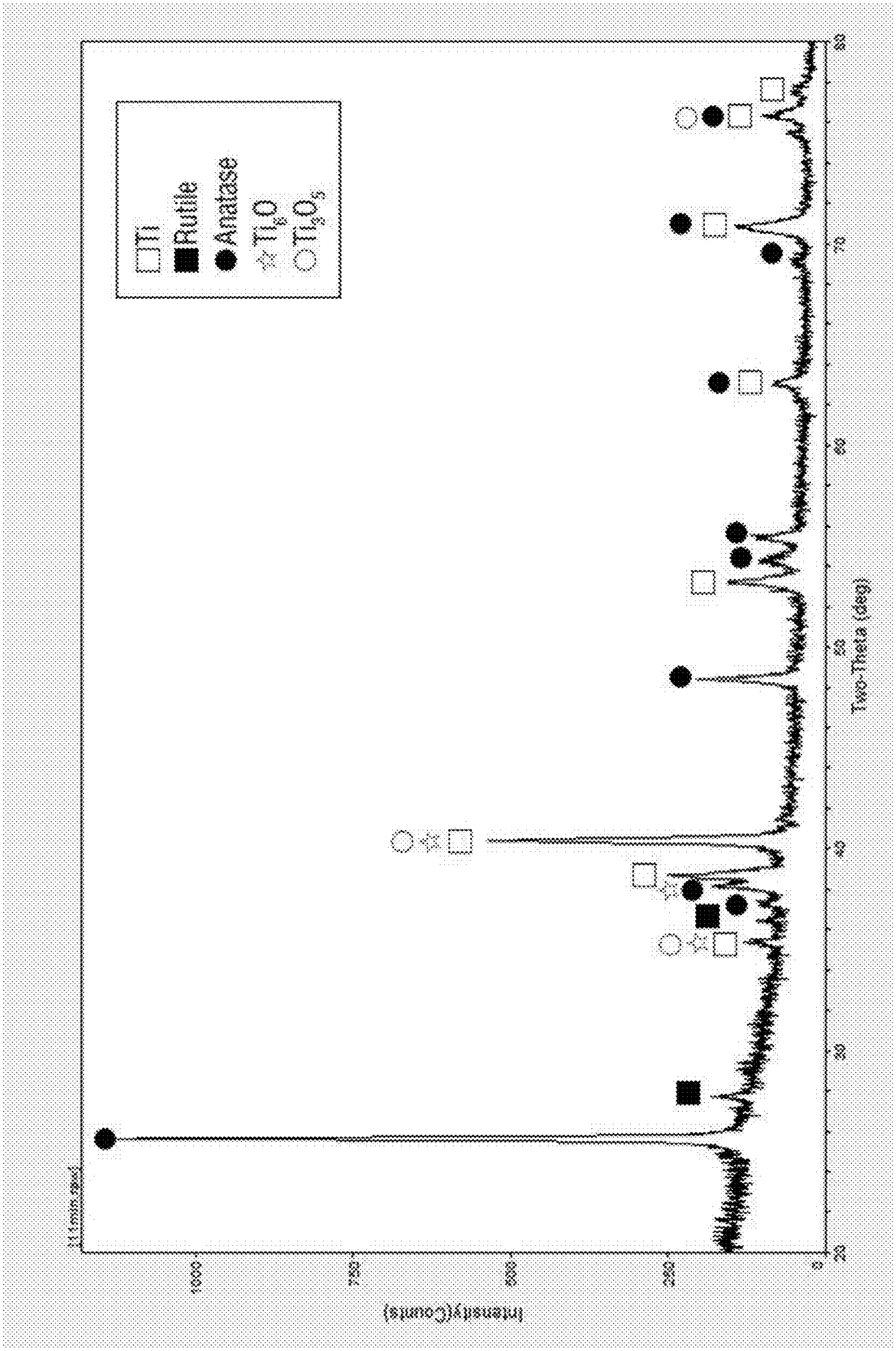
FIG. 7 shows an X-ray diffraction (XRD) of the porous layer on the surface of the titanium implant with a surface coating in a crater-like porous shape prepared in Example 1 of the present disclosure.

It was seen from the XRD pattern in FIG. 7 that the porous layer prepared in Example 1 had a weak anatase crystal phase $TiO_2$ diffraction peak and a more obvious Ti diffraction peak. The porous layer prepared by the present disclosure had a shorter voltage loading time due to the micro-arc oxidation, and the electrolyte was cooled by circulating water, such that the electrolyte during the entire micro-arc oxidation did not exceed 30° C. Therefore, the $TiO_2$ generated in the porous layer was mostly the anatase crystal phase, and there was no obvious rutile phase.

Test 5: Hydrophilicity Test

Figure 8:
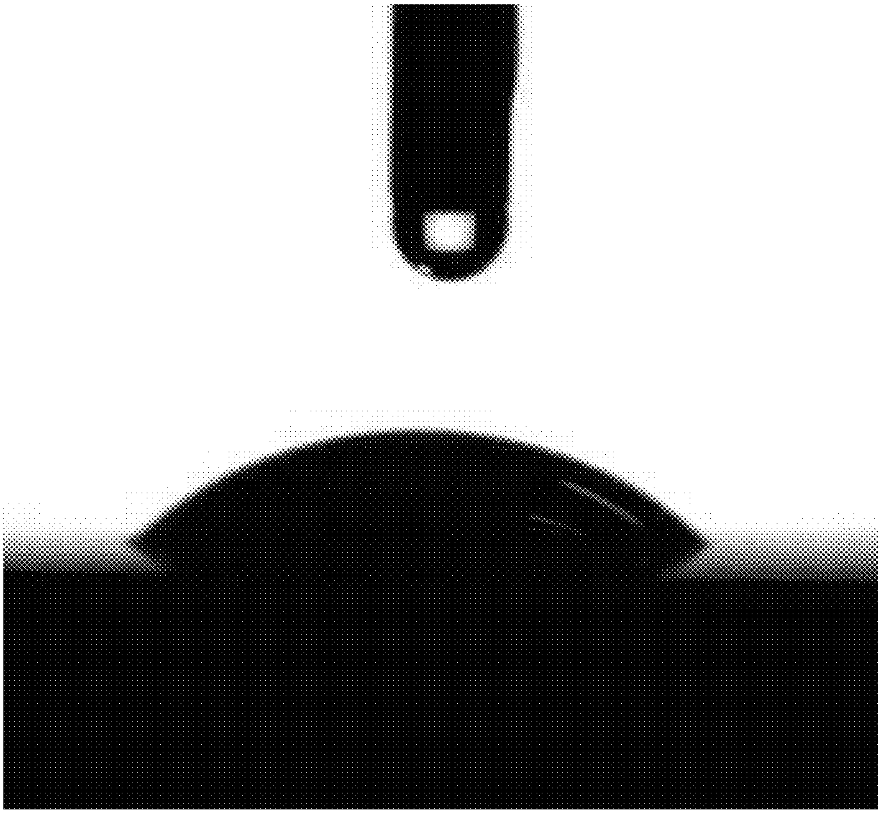
FIG. 8 shows a hydrophilic test result of the porous layer on the surface of the titanium implant with a surface coating in a crater-like porous shape prepared in Example 1 of the present disclosure.

The results of the hydrophilicity test were shown in FIG. 8.

It was seen from FIG. 8 that the porous layer prepared in Example 1 had a contact angle of (43.75±0.89)°. Studies have shown that if the surface of a material is moderately wet, that is, the value of contact angle is 10° to 80°, the surface can significantly promote the adhesion of cells. The hydrophilicity of medical pure titanium treated by micro-arc oxidation is better than that of pure titanium. Implanting the medical pure titanium prepared in Example 1 as an implant in the living body could accelerate osseointegration and shorten the healing time to a certain extent.

Test 6: Cytotoxicity Test of the Porous Layer

Bone-marrow mesenchymal stem cells (BMSCs) were isolated and cultured from the bone marrow of 4-week-old SD rats. Bone marrow was isolated from mouse tibia, and then cultured in α-medium (α-MEM, Gibco, USA) containing 10% fetal bovine serum (FBS, Gibco, USA) and 1% penicillin-streptomycin (PS, Gibco, USA). Primary cells were cultured for 48 h at 37° C. with 5% $CO_2$. The BMSCs adhered to the bottom of the culture dish were then collected. The medium was changed every 3 d. Cells between passage 3 and 6 were used for the following experiments.

Osteogenic differentiation was induced using an osteogenic medium containing 10% fetal bovine serum, 1% penicillin/streptomycin, 50 μg/mL ascorbic acid (Sigma, USA), 10 mM sodium β-glycerophosphate (Sigma, USA), and 10 nM dexamethasone (Sigma, USA). A fresh osteogenic induction medium was added every 3 d to maintain the cells.

For the determination of cell viability, all sterilized micro-arc oxidation-treated, SLA-treated, and pure-titanium samples (with a diameter=1.4 mm) were placed in a 24-well plate separately. After each sample was rinsed twice with PBS, cells were inoculated on the sample at a density of $7\times10^4$ cells/mL. Cytotoxicity was determined after 1 d, 3 d, and 5 d of culture. In proliferation assays, medium was changed every other day. After the specified incubation time, a CCK-8 dye was added to each well and incubated at 37° C. for another 2 h. Finally, an optical density (OD, n=5) was measured with a plate reader at a wavelength of 450 nm, while a blank control group was used to determine whether the cells were in a normal state and did not participate in statistical comparison. It was found that the viability of the cells in this group was normal, indicating that the cells had not mutated. A CCK-8 test result graph was obtained, as shown in FIG. 9.

Figure 9:
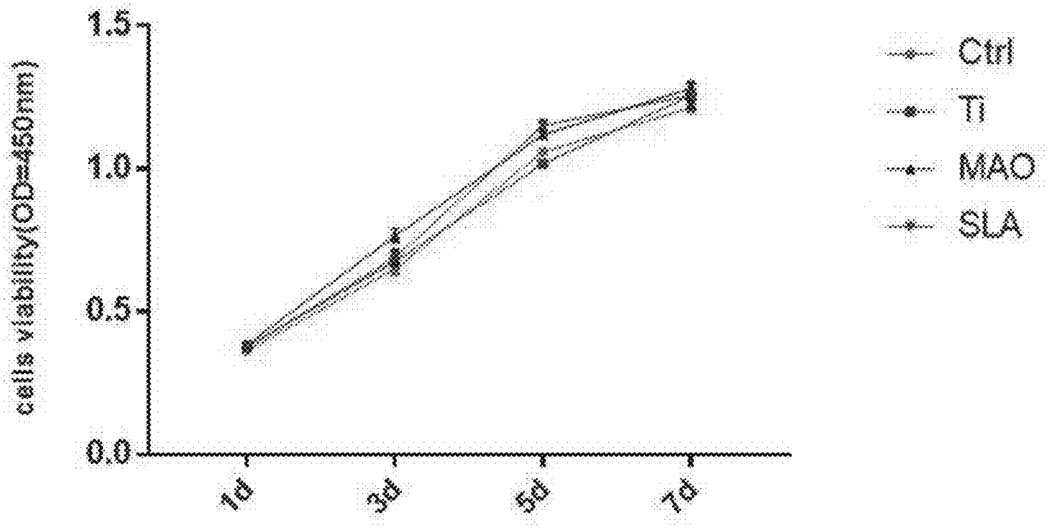
FIG. 9 shows a CCK-8 test result of the porous layer on the surface of the titanium implant with a surface coating in a crater-like porous shape prepared in Example 1 of the present disclosure.

It was seen from FIG. 9 that the cells on the surface of the porous layer formed after the micro-arc oxidation in Example 1 increased continuously with the prolongation of the culture time, and the average value of absorbance on the 1st day, 3rd day, 5th day, and 7th day increased stepwise. On the day 1, there was little difference among the experimental groups; on days 3, 5, and 7, the cell viability of the MAO-treated porous layer was significantly higher than that of pure titanium and comparable to that of SLA.

After BMSCs were co-cultured with MAO-treated porous layer for 1 d, 3 d, 5 d, and 7 d, BMSCs could proliferate on the surface of the porous layer; meanwhile, with the increase of time, the number of cell proliferation increased, indicating cytocompatibility of the MAO-treated porous layer. MAO-treated porous layer could effectively promote the proliferation of BMSCs.

Test 7: Cell Adhesion Test

BMSCs were inoculated to a 24-well cell culture plate with the micro-arc oxidation-treated medical titanium substrate (the titanium implant) prepared in Example 1 at $7\times10^4$ cells/well, and the culture was terminated on the 1st, 3rd, 5th and 7th day. The medium was removed, the cells were rinsed with PBS for 10 min, and each group of cell samples was transferred to a new 24-well culture plate, and fixated with a 4% paraformaldehyde solution for 10 min. The fixative was removed, the cells were washed with PBS for 10 min, and dehydrated with gradient ethanol solutions (30%, 50%, 70%, 80%, 90%, and 100%) for 10 min at each concentration. The samples were vacuum-dried for 3 h, sputtered with gold for 60 sec, and examined under a SEM. The test result, a microscopic view of the cell adhesion test, was shown in FIG. 10.

Figure 10:
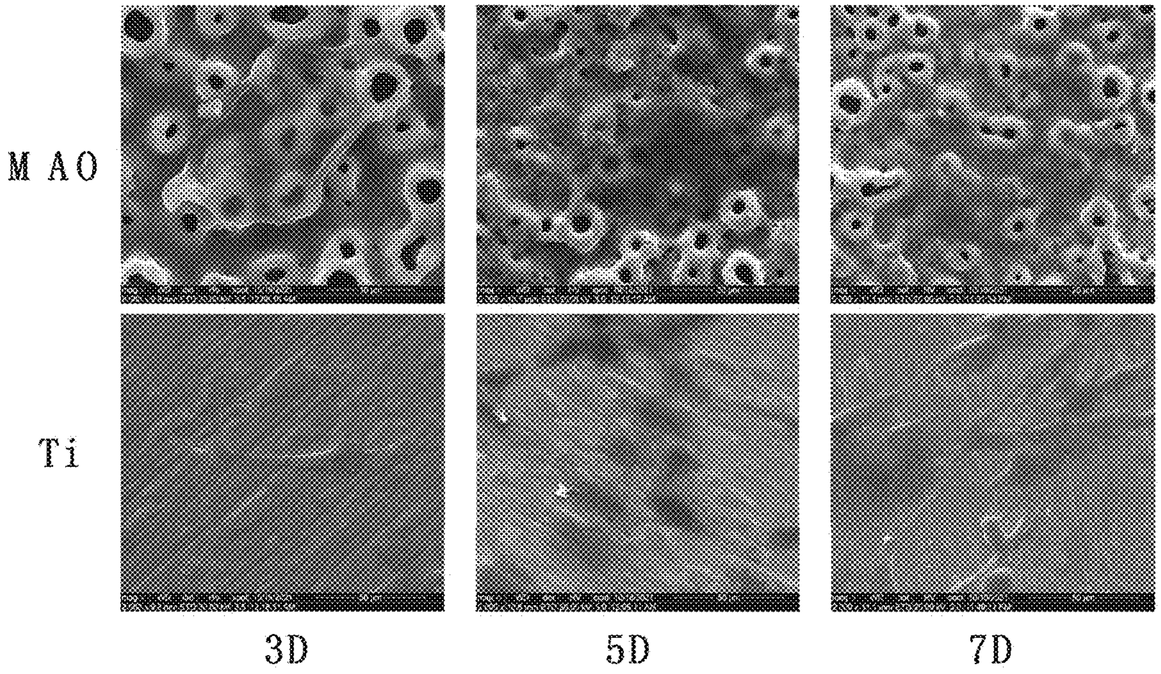
FIG. 10 shows a microscopic view of a cell adhesion test of the porous layer on the surface of the titanium implant with a surface coating in a crater-like porous shape prepared in Example 1 of the present disclosure.

It was seen from FIG. 10 that the cells on the surface of the medical titanium substrate prepared in Example 1 (the titanium implant) were well adhered, and the cells were spread flat, basically in the shape of a secretory function state, showing a triangle or star shape. Pseudopodia stretched out from the edge of the cell, which adhered to the MAO coating surface, and cell filopodia extended into the micropores. Cells adhered and spread well on the pure titanium and MAO coating surface, indicating that the medical pure titanium surface and the MAO coating surface were both conducive to cell adhesion. The cells adhered more tightly to the MAO coating surface, and spread deeply into the micropores, indicating that the surface after micro-arc oxidation was more conducive to the attachment and growth of BMSCs.

Test 8: Expression Levels of Osteogenesis-Related mRNAs (Alp, Opn, and Ocn) in BMSCs 2 mL of a BMSC suspension was implanted into a 6-well plate overnight at a density of $1\times10^5$ cells/mL. Each well was replaced with osteogenic medium for days 0 and 7. After 7 d of induction, total RNA was isolated using a Trizol (Invitrogen, USA) extraction method according to the manufacturer's protocol, and the total RNA was determined using a Nanodrop system (Thermo Fisher Scientific, USA). RT-PCR was conducted using Hieff® qPCR SYBR Green Master Mix (Shanghai Yasen). A relative gene expression level was calculated using a comparative $2^{-\Delta\Delta CT}$ method. Ctrol was set as a blank control group, Ti was set as a pure titanium sheet group, and the expression levels of mRNAs (Alp, Opn, and Ocn), as shown in FIG. 11.

Figure 11:
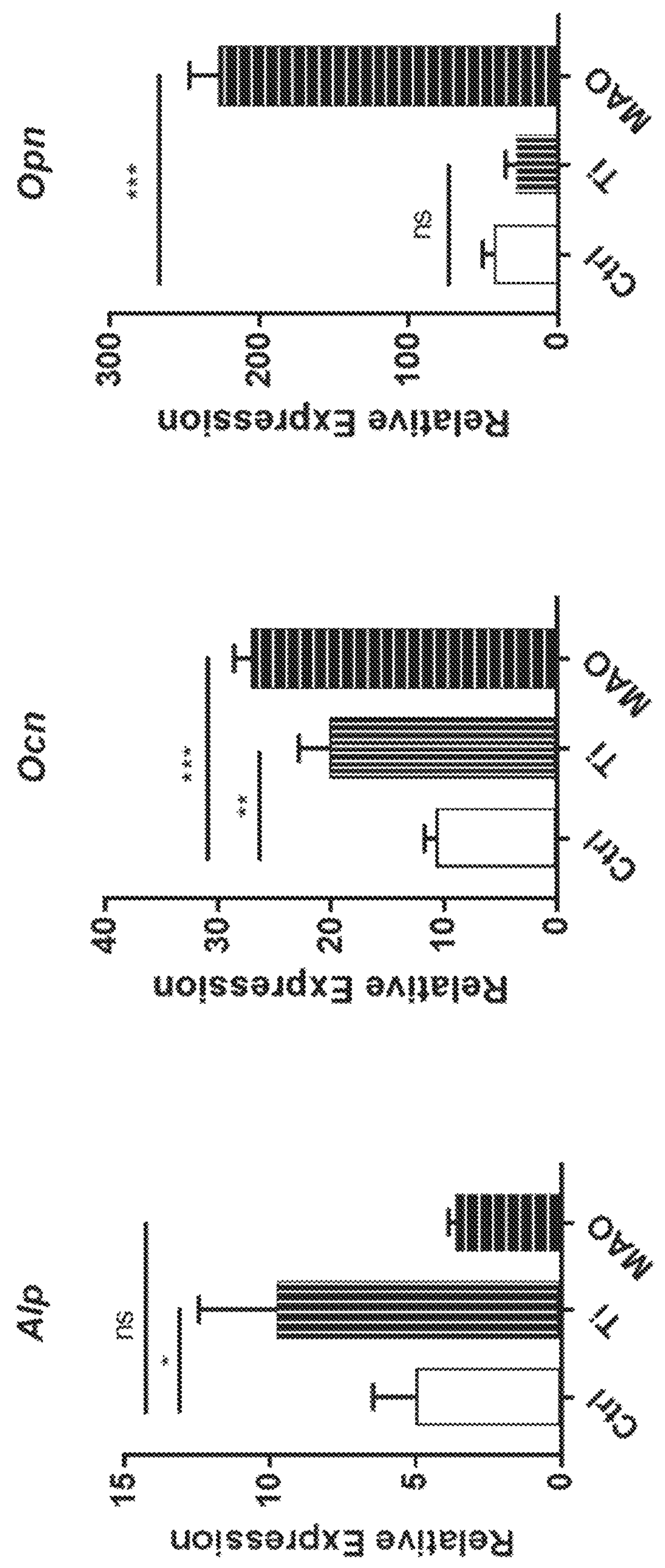
FIG. 11 shows expression levels of mRNAs (Alp, Opn, and Ocn) of the porous layer on the surface of the titanium implant with a surface coating in a crater-like porous shape prepared in Example 1 of the present disclosure.

It was seen from FIG. 11 that the micro-arc oxidation coating (porous layer) prepared in Example 1 up-regulated the expression level of ALP, OCN, and OPN-related genes, indicating that the MAO coating promoted osseointegration. The results showed that the MAO coating had an excellent osteogenic ability.

in conclusion, after being treated by the method of the present disclosure, a porous layer formed on a surface of a medical titanium substrate (the titanium implant) prepared in Example 1 can significantly enhance the adhesion, proliferation, and differentiation of osteoblasts. The porous layer prepared in Example 1 has a crater-like porous shape with a pore size of about 6 μm, which is conducive to the adhesion and growth of bone-derived cells, and has a great effect on the growth of osteoblasts; an adhesion level of the porous layer is 5B, showing a relatively-high bonding strength with the titanium substrate. The porous layer prepared in Example 1 and the titanium substrate have a bonding strength of 5.9N. The porous layer prepared in Example 1 has a thickness of 3 μm to 10 μm, where the crater-like porous shape has a convex part with a thickness of about 10 μm, and a concave part with a thickness of about 3 μm; the porous layer is mainly composed of Ti, O, P and other elements, showing an excellent biological activity. The porous layer prepared in Example 1 has medium roughness, with an Ra value of (1.399±0.008) μm. The porous layer prepared in Example 1 has a contact angle of (43.75±0.89)°.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A preparation method of a titanium implant with a surface coating in a crater-like porous shape, comprising the following steps:

(1) subjecting a titanium substrate to polishing, cleaning, and first drying in sequence to obtain a pretreated titanium substrate;

(2) conducting micro-arc oxidation by using the pretreated titanium substrate obtained in step (1) as an anode and iron as a cathode in a sodium phosphate-containing electrolyte to obtain the titanium implant with the surface coating in the crater-like porous shape; and wherein in step (2), the micro-arc oxidation is conducted at a duty ratio of 3% to 5%, wherein the sodium phosphate-containing electrolyte consists of deionized water, sodium phosphate, glycerol, and potassium hydroxide, wherein the sodium phosphate-containing electrolyte has a potassium hydroxide concentration of 2 g/L to 8 g/L, wherein the sodium phosphate-containing electrolyte has a temperature of 15° C. to 20° C., wherein the micro-arc oxidation is conducted at a current of 1.2 A to 1.4A and a working frequency of 400 Hz to 600 Hz for two minutes to four minutes, and wherein in step (1), the polishing is conducted by polishing the titanium substrate with sandpapers of 400 #, 800 #, 1200 #, 2000 #, and 3000 # in sequence.

2. The preparation method according to claim 1, wherein in step (1), the titanium substrate is a TA4 titanium alloy.

3. The preparation method according to claim 1, wherein in step (1), the cleaning is conducted by ultrasonic cleaning with acetone, absolute ethanol, and deionized water in sequence.

4. The preparation method according to claim 1, wherein in step (2), after the micro-arc oxidation is completed, a micro-arc oxidation product is subjected to rinsing and second drying in sequence.

* * * * *